United States Patent [19]

Sandstrom et al.

[11] Patent Number: 5,167,802
[45] Date of Patent: Dec. 1, 1992

[54] APPARATUS FOR SAMPLING PESTICIDE RESIDUES IN RUN-OFF WITH CONTROL OF SAMPLE PUMP AND DISTRIBUTOR VALVE

[75] Inventors: Mark W. Sandstrom, Boulder, Colo.; James C. Jelinski, Bay St. Louis, Miss.; Doreen Y. Tai, Slidell, La.

[73] Assignee: The United States of America as represented by the Secretary of the Interior, Washington, D.C.

[21] Appl. No.: 557,812

[22] Filed: Jul. 26, 1990

[51] Int. Cl.⁵ .................... G01N 1/18; B01D 21/30
[52] U.S. Cl. .................... 210/134; 73/171; 73/863.01; 73/863.21; 73/863.24; 73/864.34; 137/566; 137/625.11; 422/81; 436/39; 436/178
[58] Field of Search ........... 73/863.01, 863.02, 863.21, 73/863.23, 863.24, 863.73, 863.86, 864.34, 863.61, 863.72, 863.83, 864.91; 137/624.13, 625.11, 625.16, 565.1, 566; 210/85, 139, 141, 143, 296, 424, 511; 436/178, 180; 422/82, 101, 103, 261

[56] References Cited

U.S. PATENT DOCUMENTS

| | | | |
|---|---|---|---|
| 3,896,673 | 7/1975 | Andouze et al. | 73/864.34 |
| 3,901,084 | 8/1975 | Brailsford | 73/864.35 |
| 4,022,059 | 5/1977 | Schontzler et al. | 73/863.02 |
| 4,140,011 | 2/1979 | Krupa et al. | 73/171 |
| 4,533,643 | 8/1985 | Bell et al. | 73/863.23 |
| 4,644,807 | 2/1987 | Mar | 73/864.91 |
| 4,732,037 | 3/1988 | Daube, Jr. et al. | 73/171 |
| 4,871,675 | 10/1989 | Coupek et al. | 73/864.91 |
| 5,016,196 | 5/1991 | Nelson et al. | 73/171 |

FOREIGN PATENT DOCUMENTS

| | | | |
|---|---|---|---|
| 2641801 | 2/1978 | Fed. Rep. of Germany | 73/864.34 |
| 2277287 | 1/1976 | France | 137/625.11 |
| 54-116997 | 9/1979 | Japan | 422/103 |

OTHER PUBLICATIONS

Publication Article "Advances toward automation of pesticide residue determinations", Karlhuber et al., Analytical Chemistry vol. 47, No. 7, pp. 1094–1102, Jun. 1975.

Publication Article "Automated System for collecting water samples in proportion to stream flow rate", Claridge, New Zealand Journal of Science, vol. 18, No. 2, pp. 289–296, Jun. 1975.

Publication by Wilkinson, "An Automatic Sampler-for Intermittent Flows of Water", Instrument Practice, vol. 8, No. 5, May 1954.

Primary Examiner—Robert A. Dawson
Assistant Examiner—Joseph Drodge
Attorney, Agent, or Firm—E. Philip Koltos

[57] ABSTRACT

A water sampling device for field use operates in cleaning and sampling modes and includes a distributor valve that provides selective connection of a sample pump to a plurality of collection units so that a plurality of samples can be taken. The collection units are composed of a filter for removing particulate matter, a liquid-solid extraction cartridge, and a storage bottle. Water samples are automatically collected from a river or other water source, and then pumped immediately through the liquid-solid extraction cartridge which extracts and retains the contaminants from the water. Once the contaminants have been extracted into the cartridge, the sample is chemically stable and resistant to degradation, thereby eliminating the need for much of the special handling of samples that was previously required with field units.

13 Claims, 2 Drawing Sheets

APPARATUS FOR SAMPLING PESTICIDE RESIDUES IN RUN-OFF WITH CONTROL OF SAMPLE PUMP AND DISTRIBUTOR VALVE

FIELD OF THE INVENTION

This invention relates generally to water samplers and more specifically, to an improved water sampler apparatus for automatically capturing a sample in a liquid-solid extraction cartridge.

BACKGROUND OF THE INVENTION

An important water quality issue concerns the runoff of agricultural pesticides into lakes, streams, rivers, or other bodies of water. This runoff results in water contamination by semi-volatile organic compounds which are part of pesticide formulations. Presently used methods of sample collection for testing for organic contamination involve manually collecting large volume water samples and then transporting the samples to a laboratory for chemical analysis by the traditional liquid-liquid chemical extraction processes known in the art. Special inert containers and special handling techniques must be used to minimize contamination of the water sample and also to minimize hydrolysis reactions within the water sample between the time the sample is collected and the time it is analyzed. It will be appreciated tha such reactions can degrade the sample so that the analysis that is ultimately performed at the laboratory does not produce accurate information regarding the sample as originally taken.

There are several types of automatic samplers commercially available that process water samples by liquid-solid extraction of organic contaminants. However, these samplers are laboratory devices that are unsuitable for field use. There are also several types of automatic water samplers that are designed to sample sediment or inorganic contaminant concentrations in streams. These automatic samplers have a number of disadvantages. For example, the sample water generally comes in contact with materials in the sampler pumps and hoses which may contaminate the sample. Further, the water samples are stored in a bottle until the sampler is serviced and the sample is then transported to, and analyzed by, a laboratory so there is a problem of possible sample degradation as described above. In addition, the sample bottles are generally not made of inert materials, and thus may add to or absorb part of the organic contaminants in the sample, thereby degrading the sample or making the sample unsuitable for analysis. Further, the volume of the standard sample collected by such automatic samplers is sized for sediment or inorganic analysis and is insufficient for organic analysis Methods for manually collecting samples suitable for organic contaminant analysis also have problems associated with them. For example, such a manual method requires a person to be at the sampling location at the correct time in order to manually catch the runoff water from a rainfall. Another drawback to the manual approach is that a large number of samples must be taken in order to produce an accurate result. Other drawbacks to manual sampling include high labor costs, high shipping and handling costs, and potentially poor sample integrity.

Several examples of water samplers are disclosed in U.S. Pat. Nos. 3,969,925 (Niskin); 4,533,643 (Bell et al.); and 4,871,662 (Rosov).

The Niskin patent discloses a device for removing particulate matter from a water sample. This removal is assisted by the use of a liquid additive. The sample is captured on a filter of a particular pore size and the filter must be changed to capture material of smaller sizes. This device only enables one sample to be taken at a time, and substantial manual labor is involved first collecting the initial sample and then resetting the device.

The Bell et al. patent discloses a sampler device which uses a fluid permeable filter and in which a solvent to separate the solid part of a slurry from the liquid to be tested. This device is used to separate a water sample from a slurry which is to be discarded and requires human supervision in the taking of a sample. This device also has the restriction of being only able to take only a single sample before needing to be emptied.

The Rosov patent discloses a sampler device which uses a coarse filter to extract large particles and a fine filter, which is coated with a stabilizing agent to capture microbiological samples from a water sample. This device requires an attendant to remove a cap and fill the water sampler to collect the sample. The device cannot collect multiple samples and thus an attendant must reset the device manually before each additional sample can be taken.

SUMMARY OF THE INVENTION

20 In accordance with the invention, an automatic sampler system is provided which is portable so as to permit use thereof in the field and which enables samples to be taken and stored in the field without degradation prior to laboratory testing. The system automatically collects water samples and separates any organic contaminants from the samples in a liquid-solid extraction cartridge. Once a sample is extracted into the liquid-solid extraction cartridge, the sample is chemically stable and resistant to contamination, and thus the special handling that is required with the prior art samplers discussed above is eliminated. The water sample is collected automatically in response to a given condition such as the passage of a preselected time period or the sensing of a rainfall by a sensor, and immediately pumped through the liquid-solid extraction cartridge which extracts and preserves the organic contaminants of interest until, as stated above, the sample is ready to be transported to, and analyzed by, a remote laboratory. Sample integrity is maintained by making all wetted parts in the system from inert, non-contaminating materials. As stated, the liquid-solid extraction procedure prevents further reaction by and consequent degradation of the organic contaminants of interest.

Other features and advantages of the invention will be set forth in, or apparent from, the following detailed description of preferred embodiments of th invention.

DESCRIPTION OF THE PREFERRED EMBODIMENTS

Figure 1:
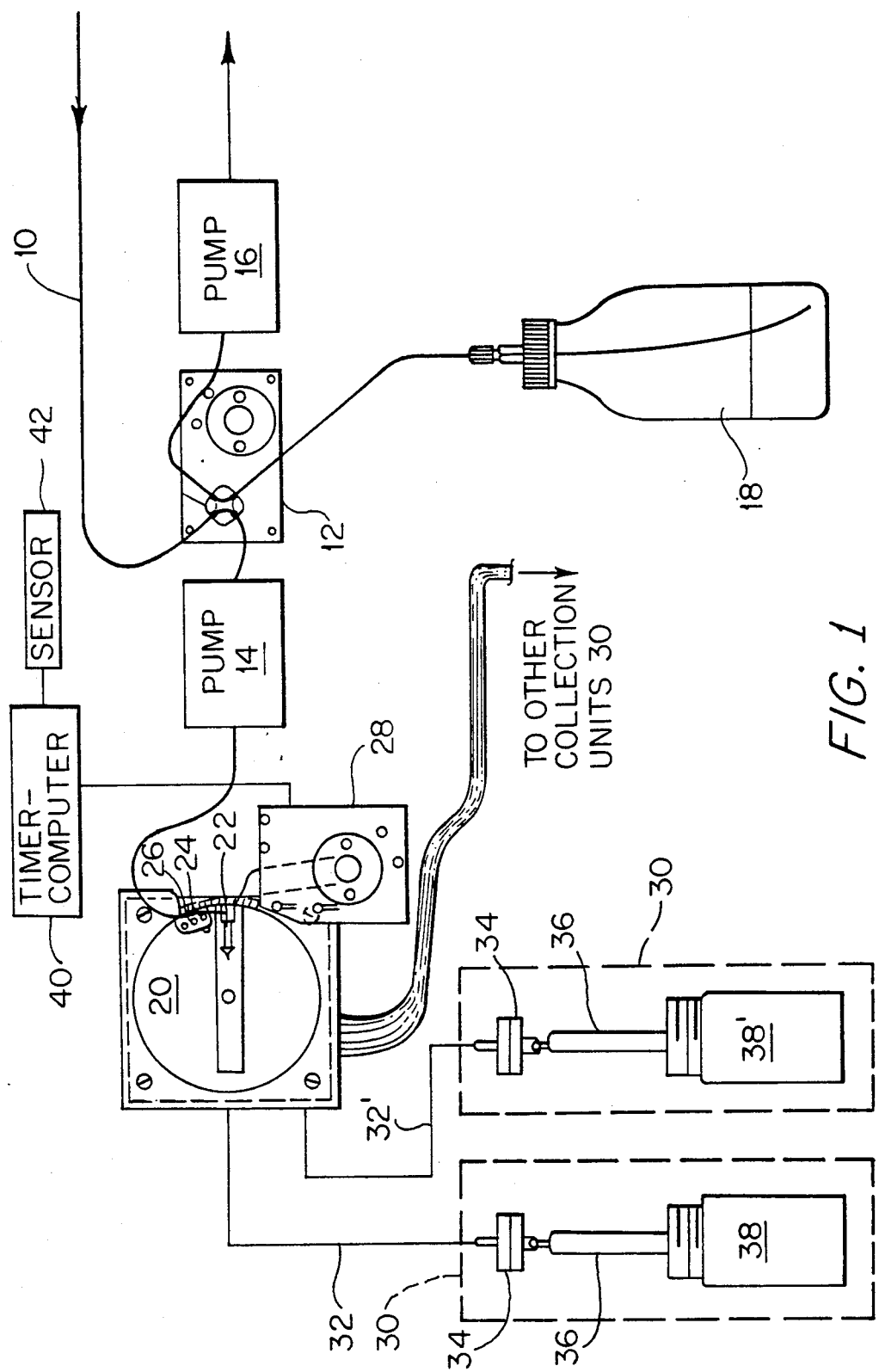
FIG. 1 is a block diagram of a sampler system constructed in accordance with a preferred embodiment of the invention.

Referring to FIG. 1, an automatic pesticide sampler constructed in accordance with a preferred embodiment of invention is shown. The sampler includes a sample inlet line 10 which is constructed of an inert material and which connects the sample inlet (not shown) with a four way valve 12. This four way valve 12 is switchable between either one of two modes of operation, viz., a clean or purge operation and a sample operation. If the four way valve 12 is in the sample mode, the four way valve 12 provides a connection between the sample inlet line 10 and a "sample" pump 14, and a further "river" pump 16 is connected to a reservoir of a cleansing solution, represented by a bottle 18 containing methanol or a similar suitable cleaning liquid. It is noted that while the sampler is in sample mode the river pump 16 is not activated. If the four way valve 12 is in the "clean" mode, the sample pump 14 is connected to the methanol bottle 18, and the river pump 16 is connected to the sample inlet line 10. Pumps 14 and 16 and four way valve 12 are conventional and can comprise commercially available units. The operation of pumps 14 and 16 and four way valve 12 is controlled by a timer/computer 40 in response to a sensor 42 as described in more detail below.

The sample pump 14 is also connected to a distributor valve 20 whose wetted parts are made of inert material. In the exemplary embodiment being considered, the distributor valve 20 has one inlet port 22 and forty eight outlet ports 24, 26. More specifically, these outlet ports comprise alternating purg outlet ports 24 and sample outlet ports 26 which are arranged around the periphery of distributor valve 20 in an alternating pattern, with the first outlet port in the illustrated embodiment being a purge outlet port 24. Each sample outlet port 26 has associated therewith a particular collection unit 30. Two such units 30 are shown in FIG. 1 and these collection units 30 are described in more detail below. A distributor valve motor assembly 28 alternately connects the inlet port 22 to either a purge port 24 or a sample port 26 depending on the mode of operation of the four way valve 12. Fluid exiting one of the purge outlet ports 24 is dumped to waste or is collected in a waste bottle. Fluid exiting the sample outlet port 26 is pumped to one of the collection units 30.

Referring to FIGS. 2 to 5, the construction distributor valve 20 is shown in more detail. Before considering this construction it is noted that the operation of distributor valve 20 is also controlled by the timer/computer 40 which receives an activating input from sensor 42 responsive to the occurrence of a particular condition such as the elapsing of a predetermined period or increment of time or an event such as the beginning of a rainfall. The sensor 42 thus provides a suitable control signal to the timer/computer 40 which, in turn, sends a signal to actuate valve motor assembly 28.

Figure 2:
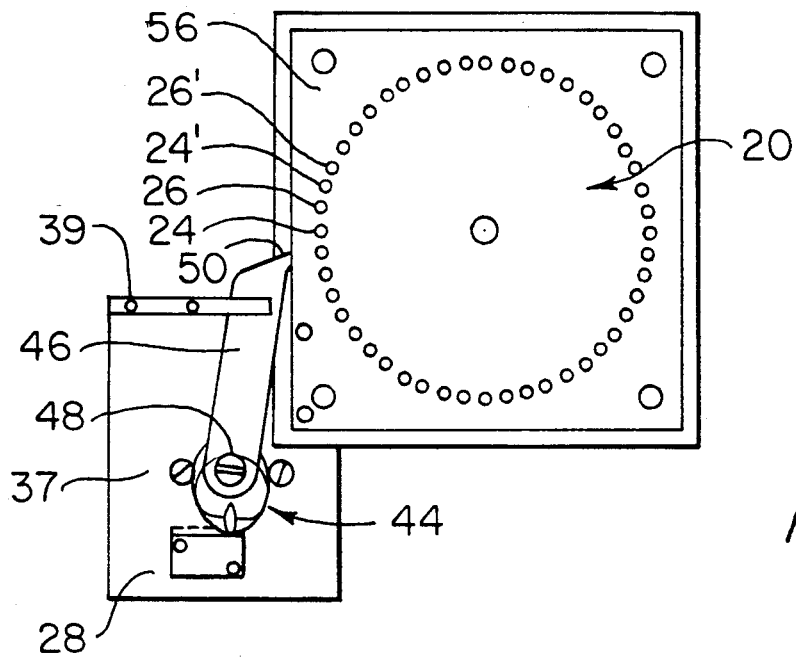
FIG. 2 is a bottom plan view of the distributor valve of the system of FIG. 1.
Figure 3:
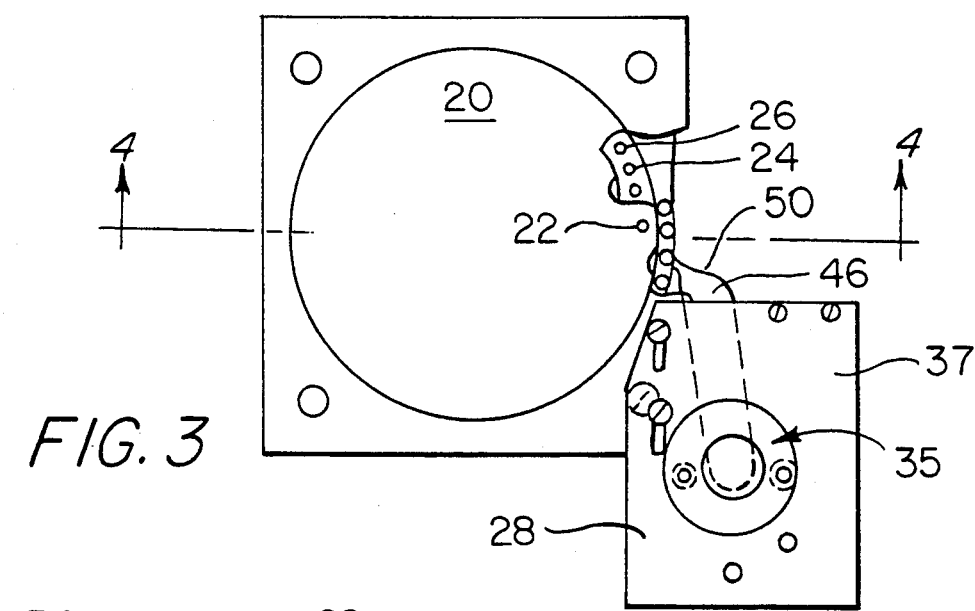
FIG. 3 is a top plan view of the distributor valve of FIG. 2, partially broken away for illustrative purposes.

As shown in FIGS. 2 and 3, the valve motor assembly 28 is composed of a motor 35 (FIG. 3) which is mounted on the top surface of a motor mount 37 of motor assembly 28 and which drives a drive pawl crank and switch cam assembly 44 (FIG. 2). The crank of assembly 44 is attached to a drive pawl 46 by a threaded screw or bolt 48. The range of movement of pawl 46 is controlled by a pawl guide 39 (FIG. 2) secured to motor mount 37. A drive motor stop switch 41 is mounted on the under surface of motor mount 37 and cooperates with the switch cam of drive pawl crank and switch cam assembly 44.

Figure 4:
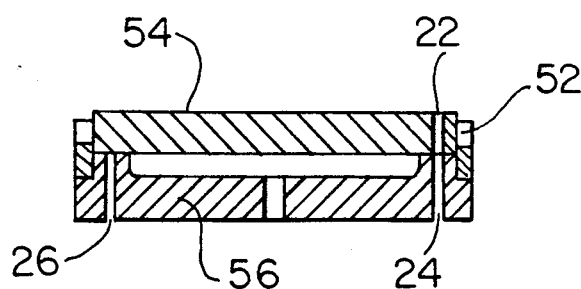
FIG. 4 is a transverse cross sectional view taken generally along line 4—4 of FIG. 3.
Figure 5:
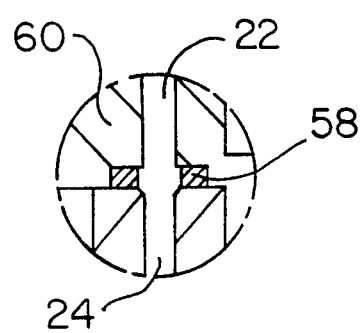
FIG. 5 is a detail of the encircled area of FIG. 3.

The pawl 46 has a finger 50 which selectively engages in one of a series of notches or detentes 52 formed in the outer peripheral edge of an upper rotating disk 54 in which inlet 22 is also formed (see also FIG. 4). The outlet ports 24, 26 are formed in the outer peripheral edge of a lower, fixed base member 56 (see also FIG. 4) and are located inboard, i.e., inwardly, of the notches or detents 52 formed in disk 54. It is noted that there is a one to one correspondence in number between the notches 52 and the outlet ports 24, 26.

An initial setup is established by aligning a purge outlet port 24 in base 56 with the inlet port 22 in disk 54 as illustrated in FIGS. 3 and 4. An o-ring or gasket 58 is provided at the lower end of inlet port 22 in contact with purge port 24. This o-ring 58 provides a watertight seal between the inlet port 22 and the purge outlet ports 24 and a raised ring portion 56a of base member 56 supports rotating disk 54.

Considering the operation of the distributor valve 20, when the timer/computer 40 sends a signal to the valve motor assembly 28, the motor 35 responds by driving crank 44 which, in turn, causes the pawl arm 46 to move so that the finger 50 engages a detent or notch 52 in rotating disk 54 to cause rotation thereof. In this way, the inlet port 22 is brought into alignment with the first sample outlet port 26, assuming that a purge outlet port 24 was originally aligned with the inlet port 22. Motor 35 is stopped when the two ports 22 and 26 are aligned by the action of motor stop switch 41. This alignment provides a connection between the inlet port 22 and a collection unit 30 through outlet port 26. Each time the timer/computer 40 signals the valve motor assembly 28 the valve motor assembly 28 will cycle between connecting the next purge port 24 to the inlet port 22 for rinsing of the sample tube and connecting the next sample outlet port 26 for delivery of the sample from the inlet port 22 to a collection unit 30 a described above.

Distributor valves of this nature are known in the art and are manufactured by Skanivalve Corp. and Chromatronics Corp.

Referring again to FIG. 1, the collection unit 30 is composed of a tube or pipe 32 which is constructed of inert material and which connects the corresponding sample outlet port 26 to a filter 34. In this regard, it will be evident that each collection unit 30 is connected to a particular sample outlet port 26. The filter 34 is designed to remove particulate matter from the sample stream so as to prevent clogging in later stages of the sampling process. The filter 34 is connected to a liquid-solid organic extraction cartridge 36 where the organic contaminants of interest are extracted from the water. Commercially available liquid-solid organic extraction cartridges 36 contain about 50 mg. of a solid inorganic matrix coated with a chemically bonded C18 organic phase. The organic extraction cartridge 36 is situated directly above a collection bottle 38 which is used for subsequent measurement of water volume.

Considering the overall operation of the pesticide sampler, in a first mode of operation, the four way valve 12 is switched to the "clean" mode or state. This causes a connection to be formed via valve 12, between the methanol bottle 18 and the sample pump 14. The sample pump is actuated by a timer/computer 40 and the methanol bottle 18 provides a methanol/water solution to the sample pump 14 which delivers the methanol solution to the distributor valve inlet 22. At this time, the distributor valve inlet 22 will be connected to a purge line outlet 24. The methanol mixture will flow through the purge line outlet 24 and will be collected in a waste bottle (not shown) or otherwise dumped, thus cleaning the system of any impurities.

After the first mode of operation of the pesticide sampler is completed, the sampler will be ready to be obtain samples when prompted by a timer/computer 40. In accordance with a second mode of operation, in the second mode of operation of the pesticide sampler the four way valve 12 is switched to the "sample" mode or state under the control of the timer/computer 40. This will cause a connection to be provided, via the four way valve 12, between the sample inlet line 10 and the sample pump 12. When a particular event occurs, e.g., the passing of a time interval or the activation of the sensor 42 in response to a rainfall, the timer/computer 40 actuates the distributor valve motor assembly 28 as described above. This causes the realignment of inlet port 22 with a sample outlet port 26 and associated collection unit 30. The sample pump 14 is then actuated via a signal from the timer/computer 40 causing river water to flow through the sample inlet line 10 into the four way valve 12. The river water is pumped by the sample pump 14 into the distributor valve inlet 22 and flows out a respective sample outlet valve 26 into line or pipe 32. The river water is filtered in filter 34 and passes to liquid-solid extraction cartr,idge 36. The river water passes through the C18 in cartridge 36 and the contaminants therein are trapped in the cartridge 36 while the water is returned in the sample bottle 38.

Continuing on with a consideration of the operation of the sampler, the automatic pesticide sampler then initiates the first mode of operation, i.e., the cleaning mode, so that another sample may be then taken. This process continues until all twenty-four samples have been collected. At this stage the amount of water in each collection unit 30 is recorded and then the water is discarded while the liquid-solid extraction cartridge 36 is sent off for testing.

Although the present invention has been described relative to specific exemplary embodiments thereof, it will be understood by those skilled in the art that variations and modifications can be effected in these exemplary embodiments without departing from the scope and spirit of the invention.

What claimed is:

1. An automatic water sampler device for obtaining and storing samples for later laboratory processing, said system comprising an inlet line means for transporting water samples collected at a sampling site; distributor valve means, including an input connected to said inlet line and a plurality of output ports, for sequentially distributing water samples received at said input port to said output ports; a plurality of collection units, individually connected to respective ones of said output ports, for collecting and storing samples from said output ports, said collection units each including a liquid-solid extraction cartridge for extracting, at the site of the water sampler device, an organic contaminant sample from said water samples; and a sample pump means for pumping water samples from said inlet line to said input of said distributor valve means.

2. The device recited in claim 1 wherein said collection units each further cmprise a filter means for filtering particulate matter from the water samples, and a storage bottle for storing said organic contaminant sample for subsequent volume measurement.

3. The device recited in claim 1 where in said distributor valve means comprises one input port and alternating purge and sample output ports.

4. The device recited in claim 3 further comprising means for sequentially connecting said input port to said output ports by a gasket or O-ring for creating a watertight seal that is tolerant of sediment in said water samples.

5. The device recited in claim 1 further comprising an automatic activating means for powering said sample pump means and for opening said distributor valve means for enabling the sampler device to take water samples while unattended.

6. The device recited in claim 5 wherein said automatic activating means comprises a sensor for sensing an occurrence of rainfall and means responsive to said sensor for controlling activation of said sample pump means and distributor valve means.

7. An automatic water sampler device for obtaining and storing samples for later laboratory processing, said system comprising an inlet line means for transporting water samples collected at a sampling site; distributor valve means, including an input port connected to said inlet line and a plurality of output ports, for sequentially distributing water samples recieved at said input port to said output ports, means for sequentially connecting said input port to said output ports by a gasket or o-ring so as to create a watertight seal that is tolerant to sediment in the water samples; a plurality of collection units, individually connected to respective ones of said output ports, for collecting and storing samples received at said output ports; and a sample pump means for pumping water samples from said inlet line to said input of said distributor valve means; and a control means, responsive to a predetermined event, for controlling operation of said distributor valve means and said sample pump means.

8. The device recited in claim 7 further comprising a reservoir for a cleaning solution and a four way valve means, for, in a first, cleaning mode, providing a connection between said sample pump and said reservoir so that said cleaning solution is pumped by said sample pump means to said distributor valve means, and, in a second, sampling mode, providing a connection between said sample pump and said inlet line means so that water samples are pumped by said sample pump means to said distributor valve means.

9. The device recited in claim 8 wherein said control means comprises an automatic activating means for powering said sample pump means, for opening said distributor valve means, and for configuring said four way valve for enabling the sampler device to take water samples and provide cleaning of said device with said cleaning solution while the sampler device is unattended.

10. The device recited in claim 7 wherein said collection units each comprise a filter means for filtering particulate matter from the water samples, a liquid-solid extraction cartridge for extracting an organic contaminant sample from said water samples, and a storage bottle in which said organic contaminant sample is stored for subsequent volume measurement.

11. The device recited in claim 7 wherein said distributor valve means comprises a single input port and a plurality of alternating purge and sample output ports.

12. The device recited in claim 7 wherein said collection units each comprise a liquid-solid extraction cartridge for extracting an organic contaminant sample from said water sample.

13. An automatic water sampler device for obtaining and storing samples for later laboratory processing, said system comprising an inlet line means for transporting water samples collected at a sampling site; distributor valve means, including an input port connected to said inlet line and a plurality of output ports, for sequentially distributing water samples received at said input port to said output ports; a plurality of collection units, individually connected to respective ones of said output ports, for collecting and storing samples from said output ports; a sample pump means for pumping water samples form said inlet line to said input port of said distributor valve means; a further pump means; a resevoir for a cleaning solution; and a four way valve means, for, in a first, cleaning mode, providing a connection between said sample pump means and said reservoir so that said cleaning solution is pumped by said sample pump means to said distributor valve means and a connection between said further pump means and said inlet line so that fresh water from the sampling site is pumped by said further pump means through said inlet line, and, in a second, sampling mode, providing a connection between said sample pump means and said inlet line so that water samples are pumped by said sample pump means to said distributor valve means.

* * * * *